(12) United States Patent
Spolski

(10) Patent No.: US 8,684,331 B2
(45) Date of Patent: Apr. 1, 2014

(54) VALVE FOR REGULATING THE FLOW OF A LIQUID

(75) Inventor: Kevin J. Spolski, Sanford, FL (US)

(73) Assignee: Bioflo, LLC, Sanford, FL (US)

( * ) Notice: Subject to any disclaimer, the term of this patent is extended or adjusted under 35 U.S.C. 154(b) by 450 days.

(21) Appl. No.: 13/105,640

(22) Filed: May 11, 2011

(65) Prior Publication Data

US 2012/0286185 A1 Nov. 15, 2012

(51) Int. Cl.
*F16K 27/08* (2006.01)
*A61M 5/00* (2006.01)

(52) U.S. Cl.
USPC .......................................... 251/367; 604/247

(58) Field of Classification Search
USPC .................................. 604/247, 534; 251/367
See application file for complete search history.

(56) References Cited

U.S. PATENT DOCUMENTS

| | | | |
|---|---|---|---|
| 2,434,167 A | 1/1948 | Knoblauch | |
| 2,667,895 A * | 2/1954 | Pool et al. ...................... | 137/528 |
| 2,792,194 A * | 5/1957 | Huck ............................... | 251/65 |
| 4,103,686 A * | 8/1978 | LeFevre ......................... | 604/249 |
| 4,160,383 A | 7/1979 | Rauschenberger | |
| 4,458,719 A | 7/1984 | Strybel | |
| 4,865,588 A * | 9/1989 | Flinchbaugh ................. | 604/129 |
| 5,114,412 A * | 5/1992 | Flinchbaugh ................. | 604/247 |
| 5,203,365 A * | 4/1993 | Velie ........................... | 137/454.2 |
| 5,330,155 A * | 7/1994 | Lechner ..................... | 251/149.6 |
| 6,030,582 A | 2/2000 | Levy | |
| 6,361,744 B1 | 3/2002 | Levy | |
| 6,488,047 B1 * | 12/2002 | Glover et al. ................. | 137/517 |
| 6,673,051 B2 * | 1/2004 | Flinchbaugh ................. | 604/247 |
| 6,752,965 B2 | 6/2004 | Levy | |
| 7,824,921 B1 | 11/2010 | Levy | |
| 7,824,922 B2 | 11/2010 | Kacian et al. | |
| 8,336,848 B2 * | 12/2012 | Foglia ......................... | 251/30.03 |
| 2002/0143318 A1 * | 10/2002 | Flinchbaugh ................. | 604/544 |
| 2007/0066965 A1 * | 3/2007 | Coambs et al. ............... | 604/533 |
| 2012/0286186 A1 | 11/2012 | Spolski | |
| 2012/0286187 A1 | 11/2012 | Spolski | |
| 2013/0204215 A1 * | 8/2013 | Spolski ......................... | 604/328 |

* cited by examiner

*Primary Examiner* — Emily Schmidt
*Assistant Examiner* — Michael J Anderson
(74) *Attorney, Agent, or Firm* — Michael L. Leetzow, P.A.

(57) ABSTRACT

A new valve for regulating the flow of liquid has two housings that are removably attached to one another. When the housings are separated, the liquid can no longer pass through the valve. A system of magnetic elements is used to cycle the flow of liquid (urine) through the valve. The valve is typically connected to an indwelling bladder catheter and the valve allows the patient to be at least temporarily disconnected from a collection bag.

16 Claims, 8 Drawing Sheets

VALVE FOR REGULATING THE FLOW OF A LIQUID

BACKGROUND OF THE INVENTION

Field of the Invention

A new design for a valve that regulates the flow of a liquid has the ability to passively regulate the flow of liquid and allows the valve housing to be disconnected, allowing movement of the person to whom the valve is connected away from a collection bag.

Many people, at home, in a hospital, and in third-party care facilities require the use of an in-dwelling bladder catheter because of a medical condition. However, being constantly attached to a bladder bag that holds the liquid (urine) is inconvenient and potentially and unnecessarily limits the person's movement and living conditions.

A new valve allows for the cyclical emptying of the bladder and allows the patient to be disconnected from the collection bag.

SUMMARY OF THE INVENTION

The present invention is directed to a valve for regulating the flow of a liquid therethrough that includes a first housing having an inlet and an outlet, a second housing removably attachable to the first housing, the second housing having an opening extending therethrough, a first magnet disposed in the first housing in a predetermined position, the first magnet being stationary relative to the housing, a second magnet disposed in the first first housing, the second magnet movable relative to the first magnet, and a sealing member disposed in the first housing adjacent the outlet, the sealing member sealing the outlet in the first housing when the second housing is disengaged from the first housing.

In some embodiments, the valve includes a resealable opening disposed in the first housing.

In some embodiments, the valve includes a vent disposed in the second housing.

In some embodiments, the sealing member includes an elastic member that engages a portion of the first housing and the second housing has a projection that engages the sealing member and compresses the elastic member when the second housing engages the first housing.

In another aspect, the invention is directed to a removable housing to engage a housing with at least one closable opening therein, the removable housing includes an outer housing having first end to engage the housing with at least one closable opening and a second end to engage tubing, an opening extending between the first end and the second end of the outer housing, a latch disposed adjacent the first end to engage at least a portion of the housing with at least one closable opening to maintain the removable housing in contact with the housing with at least one closable opening, a projection disposed at least partially within the opening, the projection extending from a middle portion of the opening toward the first end and configured to be disposed within an opening of the housing with at least one closable opening.

In yet another aspect, the invention is directed to a valve for regulating the flow of a liquid therethrough that includes a first housing having an inlet and an outlet, the inlet and outlet being in fluid communication with one another, a second housing removably attachable to the first housing, the second housing having an opening extending therethrough and in fluid communication with the outlet when the second housing is connected to the first housing, and a sealing member disposed in the first housing adjacent the outlet, the sealing member sealing the outlet in the first housing when the second housing is disengaged from the first housing.

Additional features and advantages of the invention will be set forth in the detailed description which follows, and in part will be readily apparent to those skilled in the art from that description or recognized by practicing the invention as described herein, including the detailed description which follows, the claims, as well as the appended drawings.

It is to be understood that both the foregoing general description and the following detailed description of the present embodiments of the invention, and are intended to provide an overview or framework for understanding the nature and character of the invention as it is claimed. The accompanying drawings are included to provide a further understanding of the invention, and are incorporated into and constitute a part of this specification. The drawings illustrate various embodiments of the invention, and together with the description serve to explain the principles and operations of the invention.

DETAILED DESCRIPTION OF THE PREFERRED EMBODIMENTS

Figure 1:
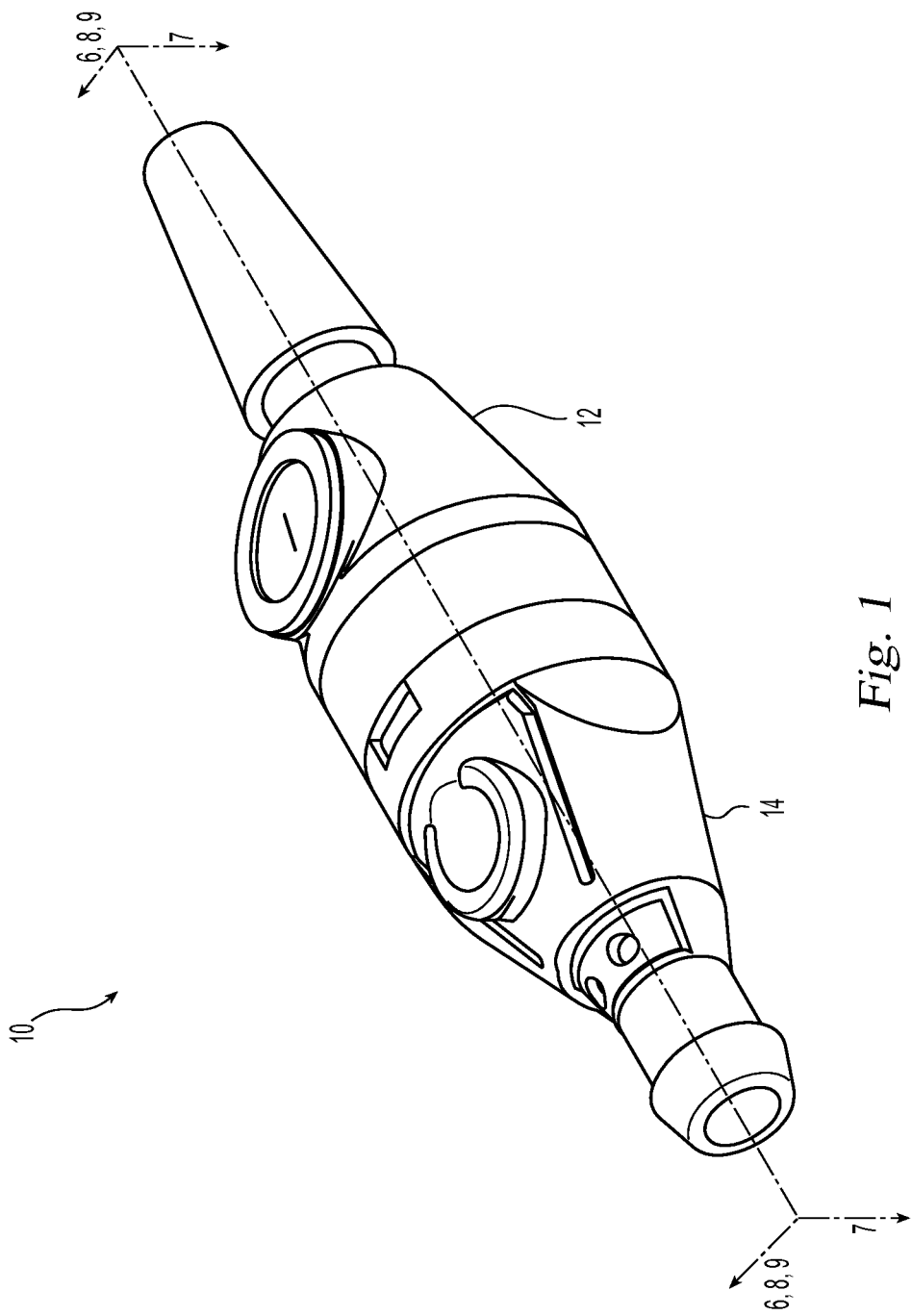
FIG. 1 is a front perspective view of one embodiment of a valve for regulating the flow of a liquid according to the present invention.
Figure 2:
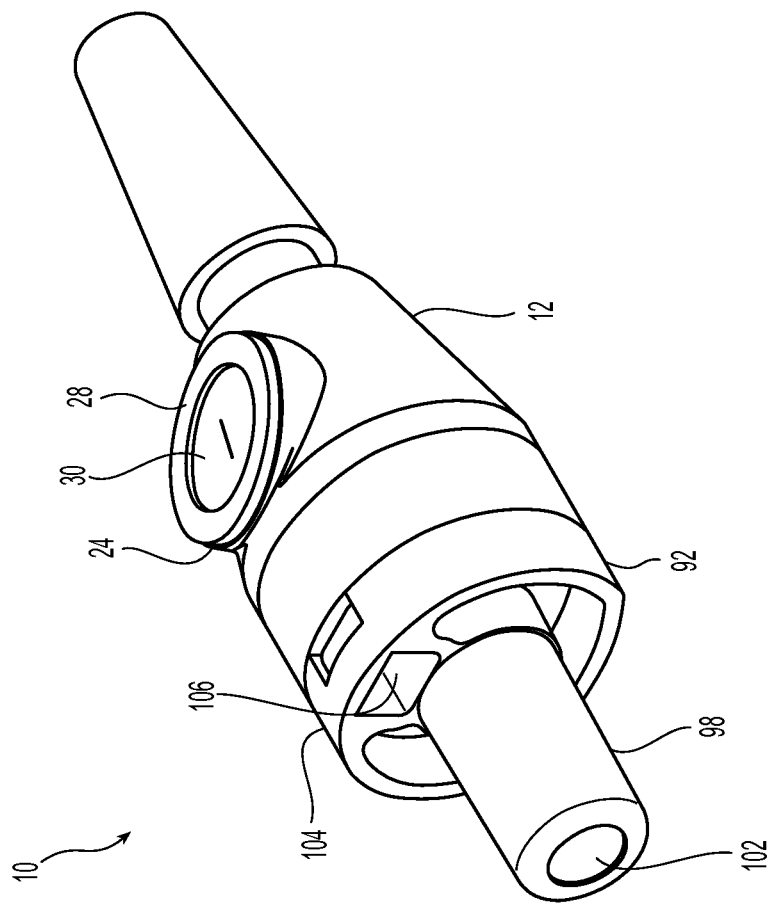
FIG. 2 is a front perspective view of the housings of the valve in FIG. 1 separated from one another.
Figure 2:
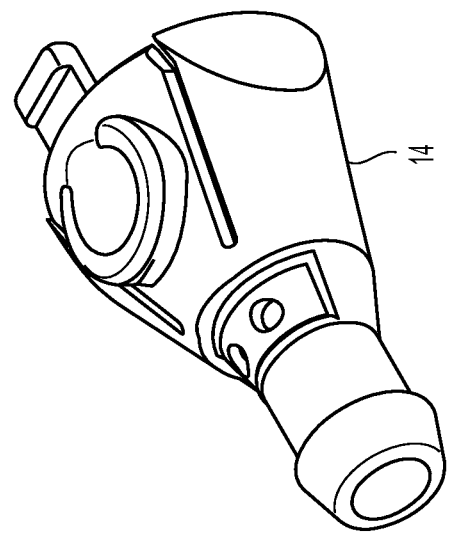
Figure 3:
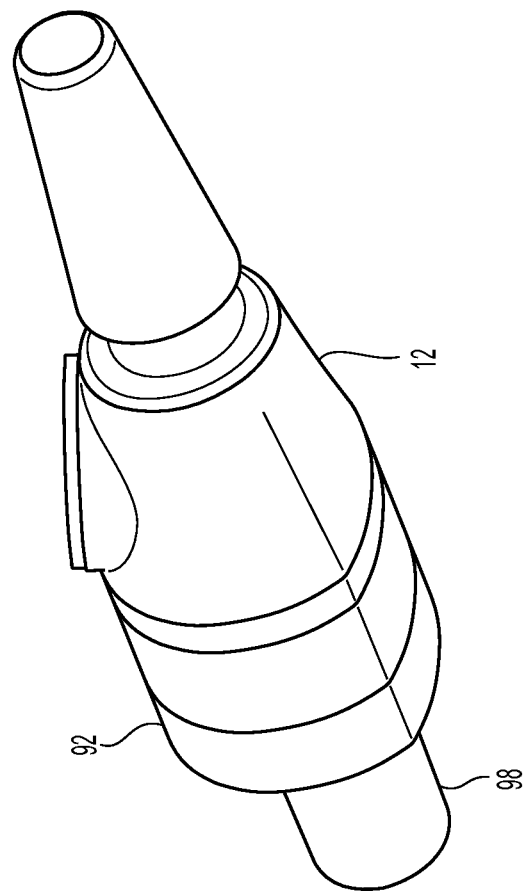
FIG. 3 is a rear perspective view of the housings of the valve in FIG. 1 separated from one another.
Figure 3:
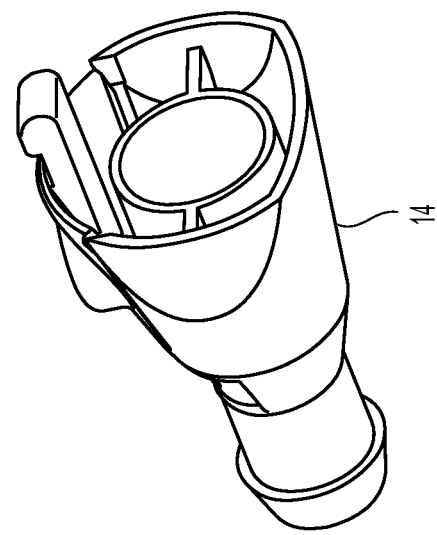

Reference will now be made in detail to the present preferred embodiment(s) of the invention, examples of which are illustrated in the accompanying drawings. Whenever possible, the same reference numerals will be used throughout the drawings to refer to the same or like parts.

One embodiment of the present invention illustrated in the figures is directed is a valve 10 for regulating the flow of a liquid. The valve 10 has a first housing 12 and a second housing 14 that is removably attachable to the first housing 12. The first housing 12 has a catheter connector 16 having a proximal end 18 and a distal end 20, the proximal end 18 of the catheter connector 16 has an inlet 22 that is configured to engage a tubing (see, e.g., FIG. 10). The inlet 22, as illustrated, has a generally smooth outer surface that increases in diameter from the end of the inlet 22 toward the remaining portion of the catheter connector 16. The inlet 22 may have any other configuration that allows for connection to tubing and still fall within the scope of the present invention. The first and second housings 12,14 are preferably made from a K-Resin SBC material.

Figure 4:
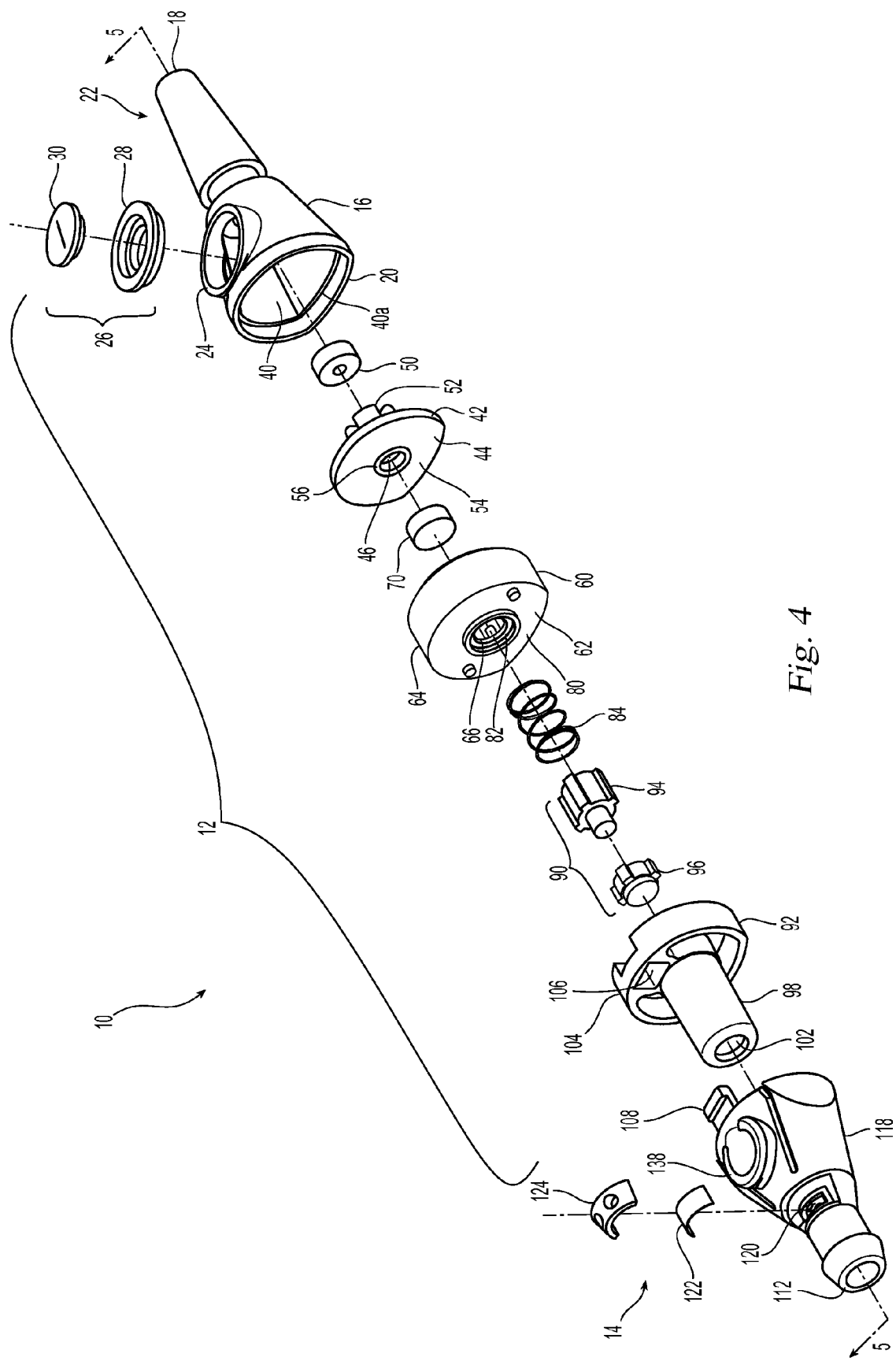
FIG. 4 is an exploded perspective view of the valve of FIG. 1.

As best illustrated in FIG. 4, the catheter connector 16 also has an opening 24 that functions as a sampling port. The opening 24 preferably has a needleless port 26. The needleless port 26 allows for insertion of a needleless syringe (not shown) to withdraw a sample of the liquid (generally urine) for testing. The needleless port 26 is preferably a resealable opening. The needleless port 26 has a main body 28 and the resealable portion 30, the resealable portion 30 may or may not have a pre-cut slit therein. It is also possible that the needleless port 26 is a single unit and not made of two different portions. The main body 28 is preferably made of polypropylene and the resealable portion 30 is preferably made of a thermoplastic elastomer, but any appropriate materials may be used.

The catheter connector 16 also has an opening 40 at the distal end 20 that is in fluid communication with the inlet 22. The opening 40 has a recessed portion 40a adjacent the distal end 20 into which a first magnet housing 42 is disposed, sealing the opening 40 of the catheter connector 16. See, e.g., FIGS. 6-9. The first magnet housing 42 has a base plate 44 that has the same configuration as the opening 40 and an opening 46 in the base plate 44 to allow the liquid to pass therethrough. On a first side 48 of the base plate 44 a first magnet 50 is secured. The first magnet 50 is secured in extensions 52 that extend from the first side 48 of the base plate 44 to keep the first magnet 50 at a predetermined distance from the opening 46 and a second magnet, which is described in more detail below. The first magnet housing 42 preferably has on a second side 54 a raised portion 56 around the opening 46. As described in more detail below, the raised portion provides a surface against which the second magnet can maintain contact to seal the opening 46.

As best illustrated in FIGS. 4 and 6-9, second magnet housing 60, also a part of the first housing 12, is attached to the first magnet housing 40 and the catheter connector 16 and extends distally from the catheter connector 16. The second magnet housing 60 is preferably generally cup-shaped, having a base member 62 and a peripheral wall 64, with an opening 66 in the base member 62 to allow the liquid to flow therethrough. Extending from the base member 62 toward the catheter connector 16 and the first magnet housing 42 are extensions 68 that slidingly hold a the second magnet 70. Preferably, there are four extensions 68, but there may be other numbers of extensions and still be within the scope of the invention. The extensions 68 also have a surface 72 to engage the second magnet 70 and prevent the second magnet 70 from moving too far distally (toward the base member 62). The second magnet 70 is drawn magnetically toward the first magnet 50 causing the second magnet 70 to engage the raised portion 56 around the opening 46, thereby closing the opening 46 and preventing the flow of liquid through the valve 10. However, when sufficient liquid is present in the opening 40 and exerts pressure on the second magnet 70 sufficient to overcome the magnetic attraction between the two magnets 50,70, then the second magnet 70 moves axially away from the opening 46 within the extensions 68 (but no farther than the surfaces 72) to allow the liquid to drain through the opening 46 (and the tubing that is inserted into bladder of a patient). When the liquid has drained away and removes this force, then the magnetic attraction causes the second magnet 70 to once again close the opening 46.

The second magnet housing 60 has on a bottom side 80 a recessed portion 82 to receive an elastic member 84 that engages and biases a sealing member 90 toward the second housing 14 in a drain end 92. While a coil spring is illustrated as the elastic member 84, any appropriate style of spring or elastic member may be used to bias the sealing member 90. The sealing member 90 preferably has two elements, a main sealing member 94 and a resilient cover member 96 that is attached to the main sealing member 94. However, the sealing member 90 may be one integral element rather than two separate elements and may be made from a single material rather than multiple materials.

The drain end 92, which constitutes the last element of the first housing 12, is attached to the second magnet housing 60 and is in fluid communication with the inlet 22 in the catheter connector 16. See FIGS. 4 and 6-9. The drain end 92 has a generally cylindrical center portion 98 in which the sealing member 90 is slidingly movable. The cylindrical center portion 98 has an inlet 100 and an outlet 102. The sealing member 90 is, as noted above, biased away from the second magnet housing 60 and toward the outlet 102 of the drain end 92. The drain end 92 also has an outer portion 104 that is secured to the bottom side 80 of the second magnet housing 60. Between the cylindrical center portion 98 and the outer portion 104 is an opening 106 into which a cantilevered latch 108 from the second housing 14 is inserted to hold the second housing 14 to the first housing 12.

The second housing 14 has a proximal end 110 and a distal end 112. The second housing 14 has an inner opening 114 that extends between the proximal end 110 and the distal end 112 and defines an inner surface 116. The second housing 14 also has a outside surface 118 and an opening 120 that extends between the outside surface 118 and the inner surface 116. The opening 120 functions as a vent to allow air to enter the valve 10 and the liquid to move through the valve 10 and into the collection bag 140. See FIG. 10. The opening 120 is preferably covered by a Tyvek covering 122 and a cover 124, which allows air to enter into the valve 10 for complete (or near-complete) emptying of the valve 10 without allowing the liquid to escape therethrough.

Figure 10:
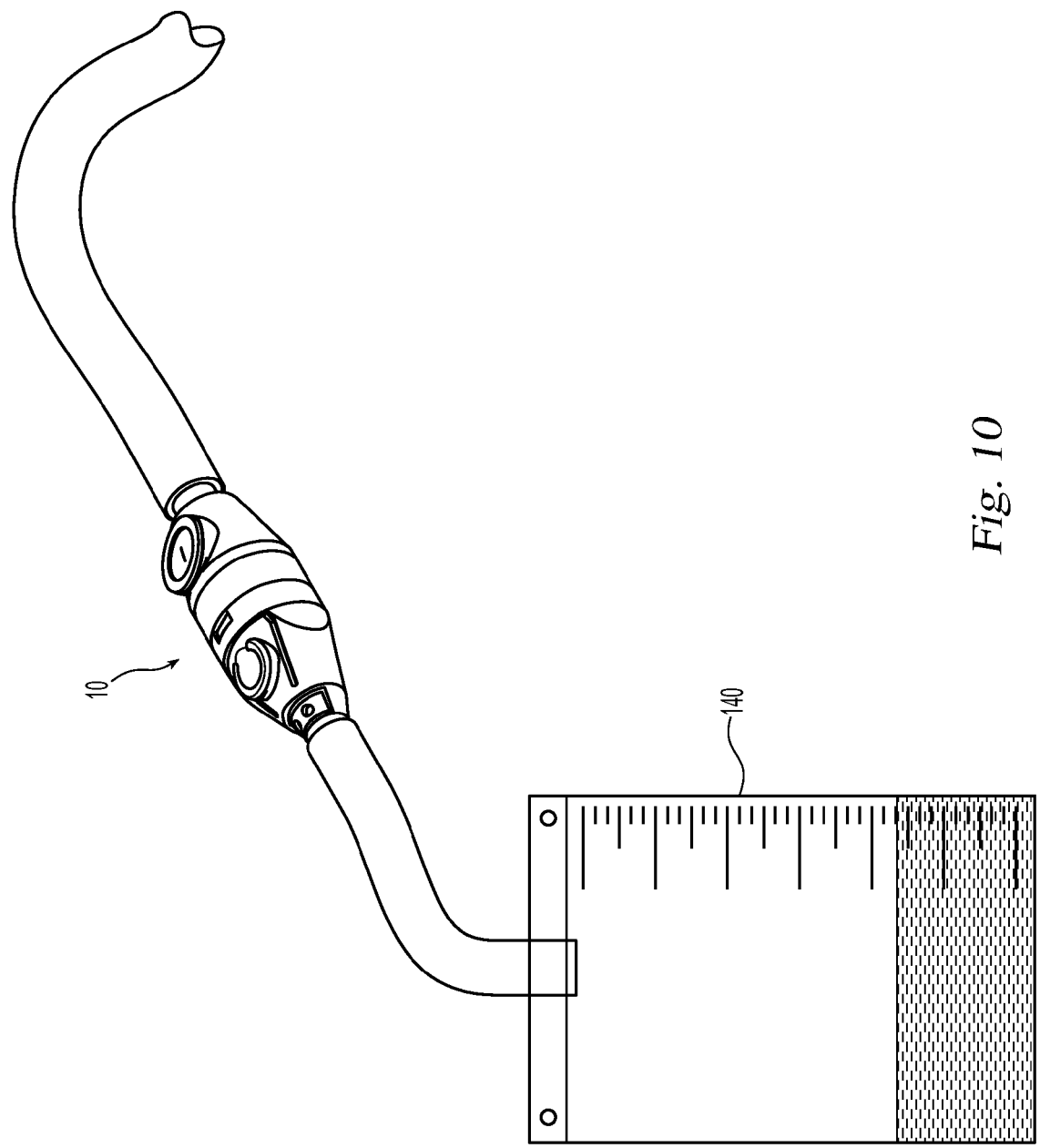
FIG. 10 is a perspective view of the valve connected to tubing on one end and a collection bag on the other end.

Positioned within the inner opening 114 is a projection 130 that extends from central portion 132 of the inner opening 114 toward the proximal end 110. The inner opening 114 also has in the central portion 132 (and preferably at the location of the distal end 134 of the projection 130) a proximally-facing surface 136. The inner opening 114 is configured and sized to receive the cylindrical center portion 98 of the first housing 12 therein and the proximally-facing surface 136 is positioned and configured such that the outer portions of outlet 102 of the drain end 92 make contact with the surface 136 and seal the valve 10 to prevent leaking when the two housings 12,14 are attached. The projection 130 is configured and sized, when the second housing 14 is connected to the first housing 12, to engage the sealing member 90 through the outlet 102 of the drain end 92 and move it axially and in a proximate direction (toward the inlet 22). This allows for the liquid to drain from the first housing 12 in to the second housing 14. Openings spaced around the bottom of the projection 130 allow the liquid to pass around the projection 130 and along the inner surface 114. Since the proximal end 110 of the second housing 14 is, by way of the latch 108, removably mounted to the first housing 12, removing the second housing 14 also removes the projection 130 from the drain end 92, allowing the sealing member 90 to seal the outlet 102, even if the second magnet 70 moves to allow the liquid to pass through the opening 46. This allows the patient to, at least temporarily, be separated from a collection bag 140, which is illustrated in FIG. 10.

Figure 5:
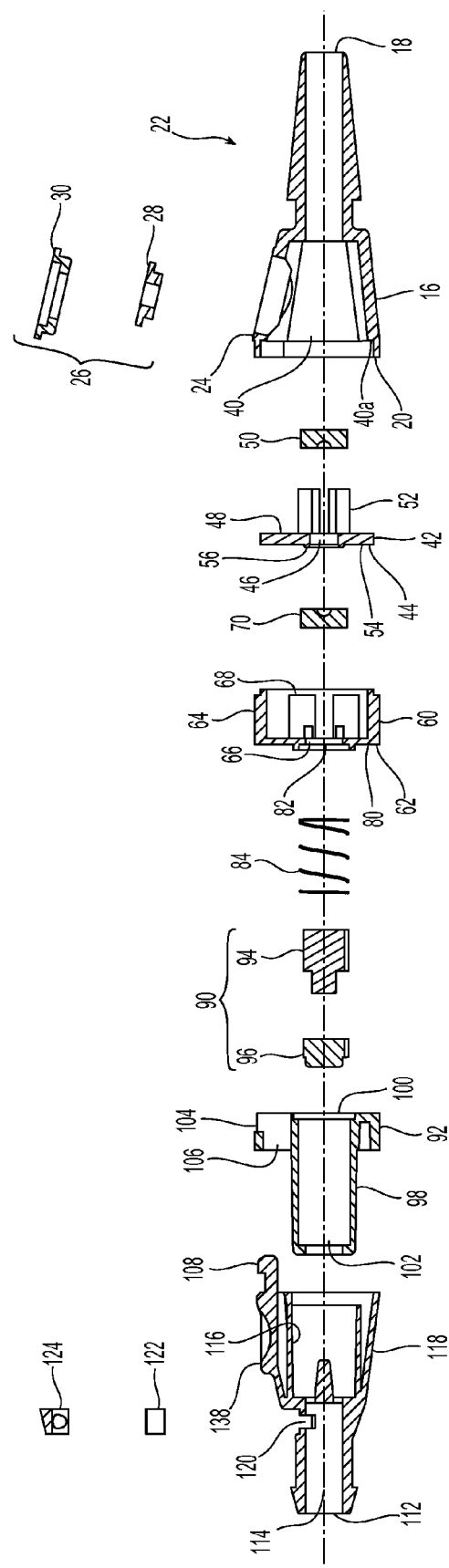
FIG. 5 is a cross sectional view from the left side of the valve in FIG. 4.
Figure 6:
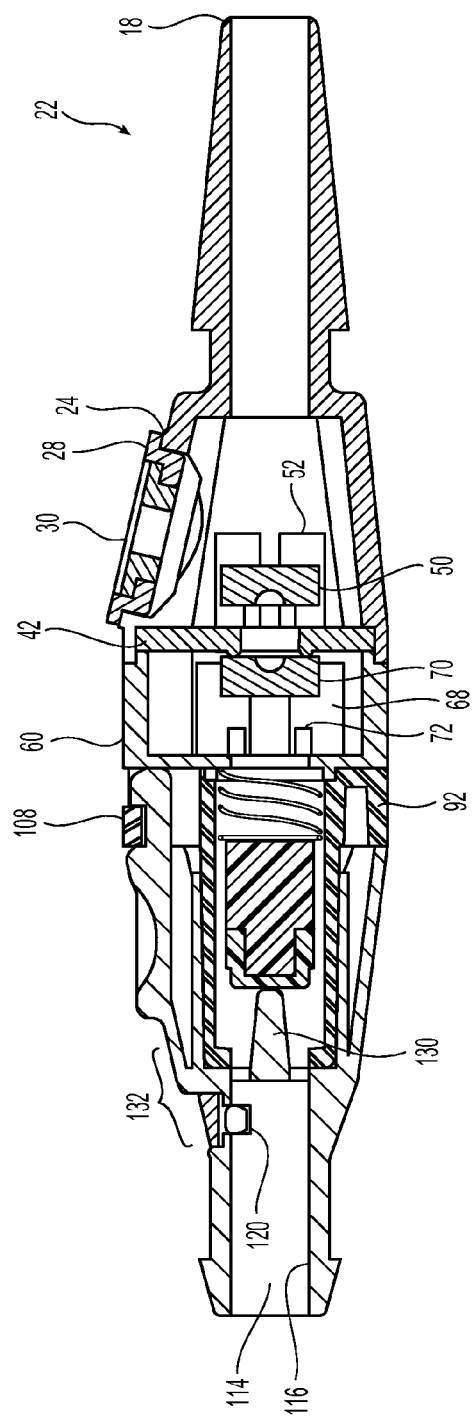
FIG. 6 is a cross section view of the valve along the line 6-6- in FIG. 1 with one magnet in a first position and sealing the valve.

As noted above, the first and second housings 12,14 are removably attached to one another by the latch 108. By "removably attached," Applicant means that the two housings 12,14 are intended to and can repeatedly engage and disengage one another without any other elements (e.g., glues, adhesives, bands, etc.), structures, or destroying any portions or parts that are intended to be used to attach housings 12,14. As best seen in FIGS. 5 and 6, the latch 108 is integral with the button 138, which when pressed then causes the latch 108 to be disengaged from the outer portion 104 of the drain end 92, and the housing 14 can be removed from housing 12. It should also be noted that due to the tight fit of the cylindrical center portion 98 in the inner opening 114, only one latch 108 needs to be used to maintain the connection between the two housings 12,14. Other types of latches and numbers of latches may also be used with the valve 10 and still come within the scope of the present invention.

Turning now to FIGS. 6-10, the operation of the valve 10 will be described in more detail. FIG. 6 is a cross sectional view of the valve 10 through the latch 108. The position of the second magnet 70 is in the proximal position, that is the second magnet 70 is sealing off the opening 46 as it makes contact with the raised portion 56 around the opening 46. As can be seen in the left side of the figure, the projection 130 has engaged the sealing member 90 through the outlet 102 since the second housing 14 is attached to the first housing 12.

Figure 7:
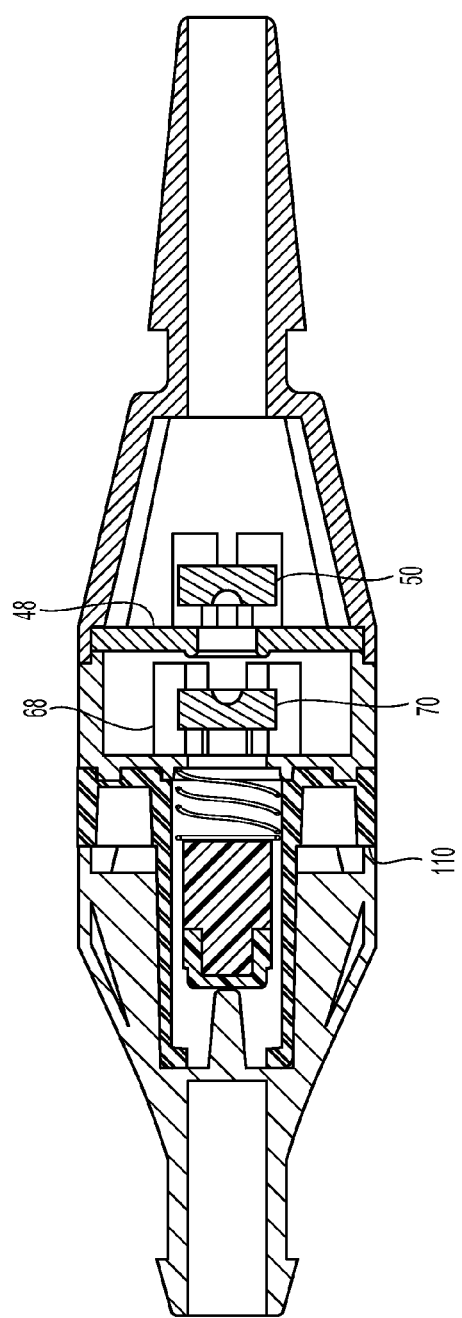
FIG. 7 is a cross section view of the valve along the line 7-7 in FIG. 1.

FIG. 7 is a cross sectional view of the valve 10 at a 90° angle to the view in FIG. 6. In this figure, the second magnet 70 is illustrated as if the liquid has exerted a sufficient force on the second magnet 70 to move it away from the raised portion 56 around the opening 46 and toward the surfaces 72.

Figure 8:
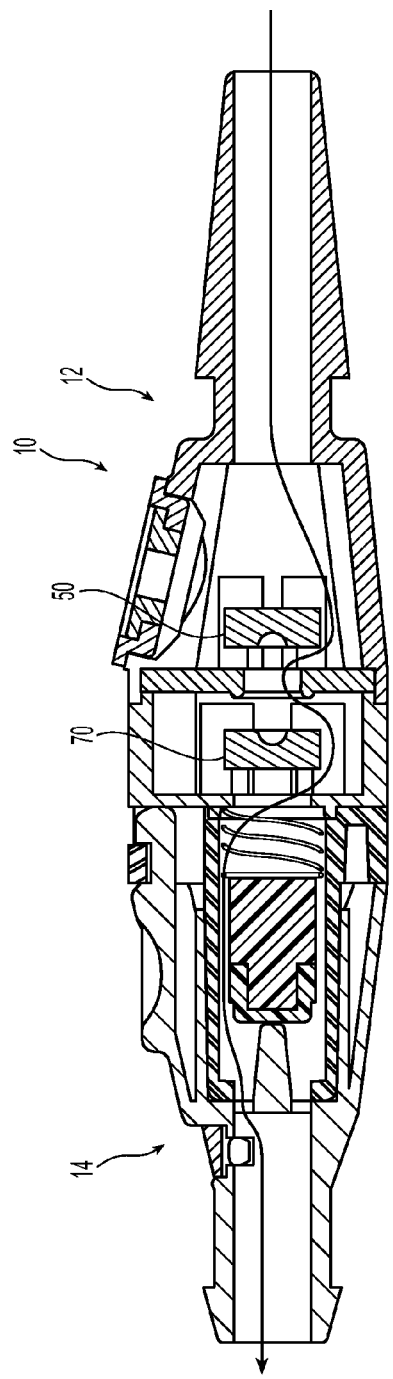
FIG. 8 is a cross section view of the valve along the line 8-8 in FIG. 1 with the magnet in a second position and allowing liquid to flow therethrough.

FIG. 8 is a cross sectional view of valve 10 in the same orientation as FIG. 6, but the second magnet 70 is is the open position and not closed as in FIG. 6. Additionally, the arrow indicates at least one path for the liquid to pass through the valve 10.

Figure 9:
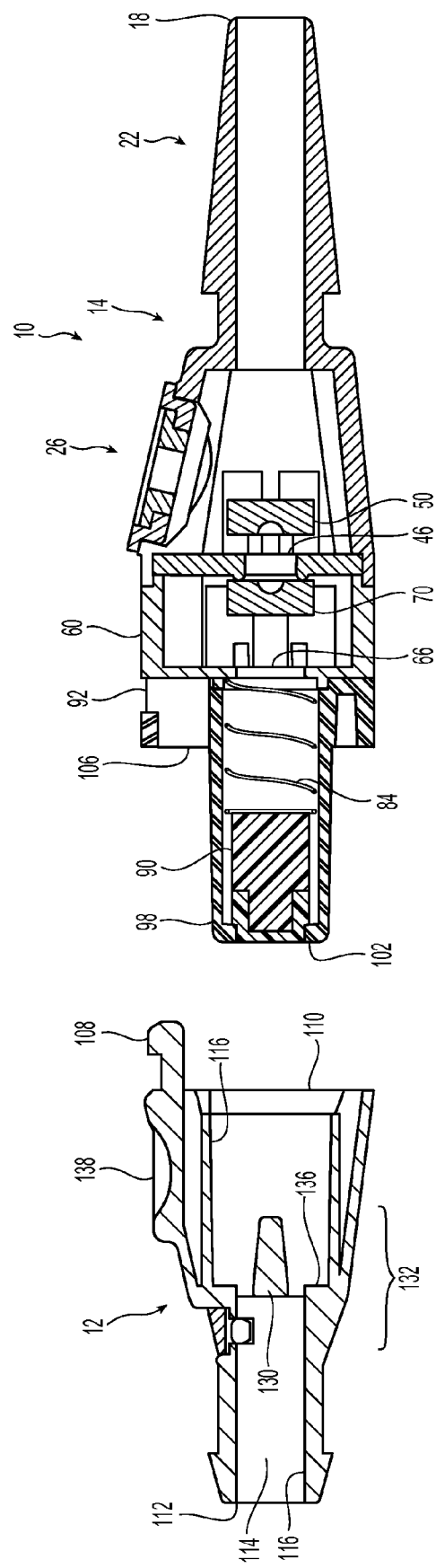
FIG. 9 is a cross section view of the valve along the line 9-9 in FIG. 2.

FIG. 9 is a cross section of the valve 10 with the first housing 12 and the second housing 14 separated from one another. In this figure, it is clear that the projection 130 no longer engages the sealing member 90, and the sealing member 90 is firmly in the outlet 102, preventing the liquid from exiting the first housing 12. This configuration allows a patient to disconnect the housings 12,14 for better mobility (or other reasons), and not have to worry about the liquid draining onto the floor or other equally distasteful places. While the second magnet 70 is illustrated as being against the raised portion 56 around the opening 46, thereby closing the opening 46, even if opening 46 were open, the liquid still would not leak from the first housing 12.

It will be apparent to those skilled in the art that various modifications and variations can be made to the present invention without departing from the spirit and scope of the invention. Thus it is intended that the present invention cover the modifications and variations of this invention provided they come within the scope of the appended claims and their equivalents.

I claim:

1. A valve for regulating the flow of a liquid therethrough comprising:
    a first housing having an inlet and an outlet;
    a second housing removably attachable to the first housing, the second housing having an opening extending therethrough;
    a first magnet disposed in the first housing in a predetermined position, the first magnet being stationary relative to the housing;
    a second magnet disposed in the first housing, the second magnet movable relative to the first magnet; and
    a sealing member disposed in the first housing adjacent the outlet, the sealing member sealing the outlet in the first housing when the second housing is disengaged from the first housing, wherein the second magnet is disposed between the first magnet and the sealing member.

2. The valve according to claim 1, further comprising a resealable opening disposed in the first housing.

3. The valve according to claim 1, further comprising a vent disposed in the second housing.

4. The valve according to claim 1, wherein the outlet of the first housing engages the opening in the second housing.

5. The valve according to claim 1, wherein the sealing member includes an elastic member that engages a portion of the first housing and the second housing has a projection that engages the sealing member and compresses the elastic member when the second housing engages the first housing.

6. The valve according to claim 1, wherein the first housing comprises:
    a catheter connector having a proximal end and a distal end, the proximal end of the catheter connector having the inlet, the inlet configured to engage a tubing;
    a first magnet housing disposed in the distal end of the catheter connector, the first magnet housing having the first magnet secured therein;
    a second magnet housing attached to the first magnet housing opposite the catheter connector, the second magnet housing having the second magnet disposed therein; and
    a drain end attached to the second magnet housing and having the outlet, the outlet in fluid communication with the inlet in the catheter connector.

7. The valve according to claim 6, wherein the second magnet is slidingly disposed in the second magnet housing and engages a portion of the first magnet housing in a first position to prevent the liquid from passing through the first housing.

8. The valve according to claim 2, wherein the resealable opening functions as a sampling port.

9. The valve according to claim 6, wherein the tubing is configured to be inserted into the bladder of a person.

10. A valve for regulating the flow of a liquid therethrough comprising:
    a first housing having an inlet and an outlet;
    a second housing removably attachable to the first housing, the second housing having an opening extending therethrough;
    a first magnet disposed in the first housing in a predetermined position, the first magnet being stationary relative to the housing;
    a second magnet disposed in the first housing, the second magnet movable relative to the first magnet; and
    a sealing member disposed in the first housing adjacent the outlet, the sealing member sealing the outlet in the first housing when the second housing is disengaged from the first housing,
    wherein the sealing member includes an elastic member that engages a portion of the first housing, and the second housing has a projection that engages the sealing member and compresses the elastic member when the second housing engages the first housing.

11. The valve according to claim 10, further comprising a resealable opening disposed in the first housing.

12. The valve according to claim 10, further comprising a vent disposed in the second housing.

13. The valve according to claim 10, wherein the outlet of the first housing engages the opening in the second housing.

14. A valve for regulating the flow of a liquid therethrough comprising:

a first housing having an inlet and an outlet;

a second housing removably attachable to the first housing, the second housing having an opening extending therethrough;

a first magnet disposed in the first housing in a predetermined position, the first magnet being stationary relative to the housing;

a second magnet disposed in the first housing, the second magnet movable relative to the first magnet; and a sealing member disposed in the first housing adjacent the outlet, the sealing member sealing the outlet in the first housing when the second housing is disengaged from the first housing, wherein the first housing further comprises:

a catheter connector having a proximal end and a distal end, the proximal end of the catheter connector having the inlet, the inlet configured to engage a tubing;

a first magnet housing disposed in the distal end of the catheter connector, the first magnet housing having the first magnet secured therein;

a second magnet housing attached to the first magnet housing opposite the catheter connector, the second magnet housing having the second magnet disposed therein; and a drain end attached to the second magnet housing and having the outlet, the outlet in fluid communication with the inlet in the catheter connector.

15. The valve according to claim 14, wherein the second magnet is slidingly disposed in the second magnet housing and engages a portion of the first magnet housing in a first position to prevent the liquid from passing through the first housing.

16. The valve according to claim 14, wherein the tubing is configured to be inserted into the bladder of a person.

* * * * *